United States Patent
Hlavacek et al.

(10) Patent No.: US 9,339,084 B2
(45) Date of Patent: May 17, 2016

(54) TIME PREDICTION SYSTEM FOR THE SAFE WEARING OF NEWLY ACQUIRED FOOTWEAR

(75) Inventors: Petr Hlavacek, Priluky (CZ); Josef Chlachula, Zlin (CZ)

(73) Assignee: UNIVERZITA TOMASE BATI VE ZLINE, Zlin (CS)

( * ) Notice: Subject to any disclaimer, the term of this patent is extended or adjusted under 35 U.S.C. 154(b) by 494 days.

(21) Appl. No.: 13/981,918

(22) PCT Filed: Jan. 25, 2012

(86) PCT No.: PCT/CZ2012/000008
§ 371 (c)(1),
(2), (4) Date: Aug. 7, 2013

(87) PCT Pub. No.: WO2012/103857
PCT Pub. Date: Aug. 9, 2012

(65) Prior Publication Data
US 2013/0332107 A1    Dec. 12, 2013

(30) Foreign Application Priority Data
Jan. 31, 2011   (CZ) .................................... 2011-53

(51) Int. Cl.
| | |
|---|---|
| A43D 1/02 | (2006.01) |
| A61B 5/107 | (2006.01) |
| A43B 3/30 | (2006.01) |
| G06Q 30/06 | (2012.01) |
| G06Q 10/04 | (2012.01) |
| G06Q 30/02 | (2012.01) |

(52) U.S. Cl.
CPC . *A43D 1/027* (2013.01); *A43B 3/30* (2013.01); *A61B 5/1074* (2013.01); *G06Q 10/04* (2013.01); *G06Q 30/0627* (2013.01); *G06Q 30/0281* (2013.01)

(58) Field of Classification Search
CPC ........... A43D 1/027; A43D 1/00; A43D 1/02; A43D 1/08; A43D 3/30; A61B 5/1074; G06Q 10/04; G06Q 10/063; G06Q 10/0639; G06Q 10/06395; G06Q 10/0838; G06Q 30/0281; G06Q 30/0623; G06Q 30/0627; G06Q 30/0631
See application file for complete search history.

(56) References Cited

U.S. PATENT DOCUMENTS

2003/0110095 A1 * 6/2003 Danenberg ............... A43D 1/02
                                                     705/26.64
2007/0011173 A1    1/2007 Agostino

* cited by examiner

Primary Examiner — Toan Le
(74) Attorney, Agent, or Firm — Andrew Wilford

(57) ABSTRACT

The device relates to a system for predicting the period for children to safely wear newly acquired footwear without the risk of damage to their growing feet, which is directly applicable in shoe shops (at their computer cash registers). The essence of the solution for a system for predicting the period for children to safely wear newly acquired footwear rests in the fact that it contains an input module measuring foot length and input of information about the age of the monitored child to which is linked a model for predicting the growth of the child's foot by applying the laws of growth, possibly also including genetic and local influences, connected to a comparative and inferential module establishing the predicted course of growth in foot length of the monitored child, to which is then linked an output module designating the nearest date for the necessary replacement of shoe size for the monitored child.

6 Claims, 1 Drawing Sheet

TIME PREDICTION SYSTEM FOR THE SAFE WEARING OF NEWLY ACQUIRED FOOTWEAR

CROSS REFERENCE TO RELATED APPLICATIONS

Figure 1:
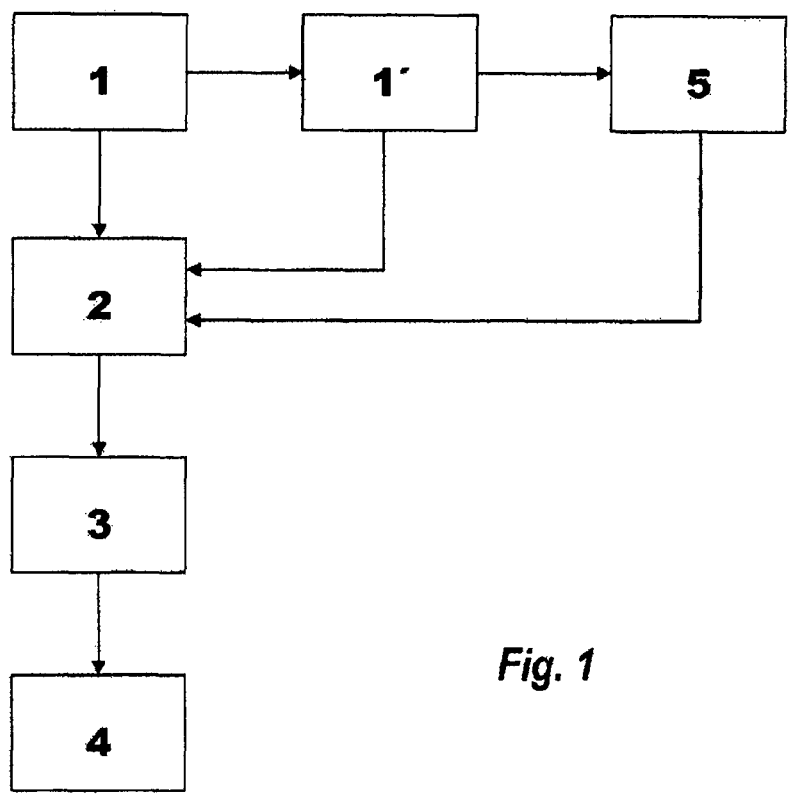

This application is the US-national stage of PCT application PCT/CZ2012/000008 filed and claiming the priority of Romanian patent application PV2011-53 itself filed 31 Jan. 2011.

TECHNICAL FIELD

The device relates to a system for predicting the period for children to safely wear newly acquired footwear without the risk of damaging their growing feet, which is directly applicable in shoe shops (at their computer cash registers) with universal use for the circle of their customers. In a non-forced form (on a voluntary basis), it enables them to inform parents when the foot of their child will have grown to a size for which the original shoe size will no longer fit and may be the source of irrevocable deformities.

PRESENT STATE OF TECHNOLOGY

The requirements for respecting special principles during the construction of children's footwear already appeared in Europe practically in the first years following the Second World War. This was related to the contemporary low consumption of footwear and the first knowledge emanating from doctors and orthopedists. As early as 1949, the German orthopedic association submitted a proposal for the systematic resolution of minimum requirements for healthy children's footwear. In 1952, the first measurements and observations of the healthy state of children's feet were conducted. In 1960, a working circle was established, which brought together representatives of manufacturers of footwear, lasts and sales of shoes in the Socialist Republic of Germany. Initially, this group emphasized as a goal merely support for the production of healthy, non-harmful footwear and the publicity of healthy footwear for children and youth. The originally formulated principles were publicized at the first expanded working meeting of interested institutions in 1965 and after revision, again in 1969, when there also occurred a renaming of the entire project to WMS (the name is taken from the recommendation of three shoe widths for each shoe size manufactured:

Weit, Mittel, Schmal, or Wide, Medium, Narrow).

The main goal of WMS is a quality selection of healthy, non-harmful children's footwear (manufactured in three widths on the basis of a standardized size and width system of marking. This standardization must facilitate a suitable selection of footwear—in WMS shops they offer a remarkable and non-binding service to customers in repeated measurement of children's feet (while using a WMS measuring instrument) throughout the entire period of their growth. The target of this system then is for it to be applied during the sale of shoes, but has its base in using the correct dimensional standards for lasts for serial production of children's shoes. The bases are included in tables depicting the distribution of sizes and widths of shoes according to the child's age. Regularly organized are extensive measurements that after processing are added to the summary of results from previous measurements and by comparing these it can be determined whether or not there are any observable significant deviations.

Overall, this was in the context of the so-called Days for Measuring Children's Feet (WMS—Kinder—Fuss-messtagen) measuring nearly 2 million children's feet, whereas in the period from 1982-1991, only 43% of observed feet were marked as adequate and 57% were marked as inadequate. Smaller shoes were found in 49%, of which by one number 36% (the authors of the study admit that half of this amount, i.e. 18% may be probably acceptable due to the inaccuracy of the measurement and the relatively low values of the toe overhang into the range of toe excess. Another 11% of children, however, used footwear 2 sizes smaller, 2% of children by 3 sizes and 0.2% of children used footwear even smaller by 4 sizes (note: the above value of 0.2% represented in absolute number nearly 3500 children). Opposed to this, only 8% of children wore shoes that were too large.

Despite the unification efforts in the context of the EU, the approach in individual European countries to the issue of children's footwear differs significantly, not only from the standpoint of the critical evaluation of fashion and materials but also in the matter of the significance of sizes and widths of footwear. This problem was resolved also in the context of the so-called "hearings" in the European parliament, when the Euro-representative Zuzana Roithova (elected to the European parliament in 2004) invited the newly designated commissioner for health and consumer policy, John Dallim of Malta, to resolve the issue of protecting children against dangerous products imported into the EU primarily from Asia. Roithova wants this to be one of the main priorities of the new Commission.

Among European countries with advanced footwear industries and with well-known research facilities, France is in the lead. Although there is a large consumption of children's footwear, even here there have appeared disturbing reports in the professional press about the adverse effects of wearing inappropriate footwear.

In the nineteen nineties, there was a significant shift in the production of footwear from the industrially developed countries to the region of the Far East. This has been caused by a significant (and continuously increasing) difference in costs for labor. In 2009, 67% of the shoes produced in the world were manufactured in China. At the same time in these countries there are no educational institutions, independent technical laboratories, a system of norms (regulations) and the possibility for objective assessment of utility characteristics. The main motive in the countries of the Far East is to produce shoes that will be sold in Europe (America or other parts of the world). Footwear imported from the countries of the Far East, without a doubt, is less expensive in comparison with footwear produced in operations of European footwear companies. This situation has resulted in European markets receiving children's footwear in shape (proportion), structurally inappropriate for the Central European shape (proportionality) of children's feet. Changes in the structure of shoe sales has reduced the requirements on the level of qualifications for personnel and currently it is frequently impossible to obtain the necessary information about the optimal parameters of offered children's footwear and the actual risks of the possible occurrence of deformities.

This situation is made more complicated in that currently there are still no products that would comprehensively resolve the issue of predicting the period for children to safely wear footwear without the risk of damaging the growing feet of children—not even at the level of a theoretical model, software or instrument resolution. At more academic sites of European as well as global universities, only unique cases are known in this direction for the processing of simple parts of growth models, which take into consideration the results of currently processed studies analyzing the laws of growth for children including children's feet.

Generally, it is possible to divide the ideas of professionals on the significance of factors affecting the healthy development of children's feet into two groups:

The first group consists primarily of professionals from German-speaking countries. Emphasized in their recommendations is the issue of "qualified sales." This originates from the assumption that qualified sales based on the precise measurement of the feet of child customers and the selection of footwear constructed according to their rules, may achieve the greatest degree in reducing deformities.

The second group consists of former East Bloc countries (Czech Republic, Poland, Hungary) in which commissions had already been established administratively to look into the rules for construction of children's footwear. Here, the emphasis is on laboratory certifiable characteristics of footwear that are derived from historical ideas and experience. Notwithstanding, there are no complex studies showing (guaranteeing) a reduction in the occurrence of deformities to children's feet on the basis of violations of measurable characteristics of shoes.

Both systems are imperfect in comparison with the need for a solution to the issue on the market, because they do not take into account the individual speed of growth in children's feet and they are also not able to evaluate the actual status in the difference between the length of newly purchased shoes and the actual foot length. At the same time, in the area of applied anthropology, there are studies that are engaged with the laws of children's growth. Knowledge from these studies are a starting point for the newly proposed system for predicting the period for children to safely wear newly acquired footwear without the risk of damaging their growing feet according to the device. The goal was to develop a special system for data collection and evaluation that would enable the establishment of the period during which it is possible to safely wear newly purchased shoes for growing feet. Whereas the period for safe wear will be established more precisely according to empirical data.

ESSENCE OF THE DEVICE

The essence of the solution for a system for predicting the period for children to safely wear newly acquired footwear (without the risk of damaging their growing feet) rests in the fact that it contains an input module measuring foot length and the input of information about the age of the monitored child to which is linked a module for predicting the growth of children's feet by implementing laws of growth, or also including genetic and local influences, connected with a comparative and inferential module establishing the predicted course of foot length growth of the monitored child to which then is linked an output module designating the nearest date for the necessary replacement of shoe size for the monitored child.

By implementing the laws of growth in the prediction module, the growth model for a child's foot may based on the Carlsberg growth model, particularized into the form of an empirical model originating from analyses of the length of the feet of children in relation to age, conducted at a group of at least 2000 children aged from 3 to 18 years. As an additional beneficial parameter, this empirical model may include the child's parent's foot length.

The input module measuring foot size and the input of information about the age of the monitored child may beneficially contain a submodule for data storage connected to the prediction module for growth in children's feet.

Furthermore, this is advantageous and useful if the growth model for children's feet implemented in the prediction module is continuously revised by inputs from the submodule of genetic influences, the inputs of which include in particular the parameters of the child's parent's foot length, possibly also the continuously revised outputs of the submodule for local impacts connected to the submodule for data storage of the input module.

Data about the foot lengths of the parents of the monitored (evaluated) children could also be a benefit for further input for the comparative and inferential module establishing the predicted course of foot length growth of the monitored child.

Benefits of the solution according to the device are on several levels:

user system—shoe shops—acquire an easy tool for optimal selection, or recommendations for correct shoe size;

customers who purchase shoes within the recommended term, will be able to optimize the selection according to the longest possible period for wear in regard to the speed of growth of the child's foot;

creators (administrator) of the system obtain the possibility to centralize measured data and to take advantage of it for more precise modification of the prediction model for the local population;

from a health standpoint, using the system contributes to the reduction in the main causes of damage to children's feet due to deformation invoked by the unconscious wearing of small, dimensionally inappropriate shoes.

OVERVIEW OF IMAGES IN DRAWINGS

Figure 2:
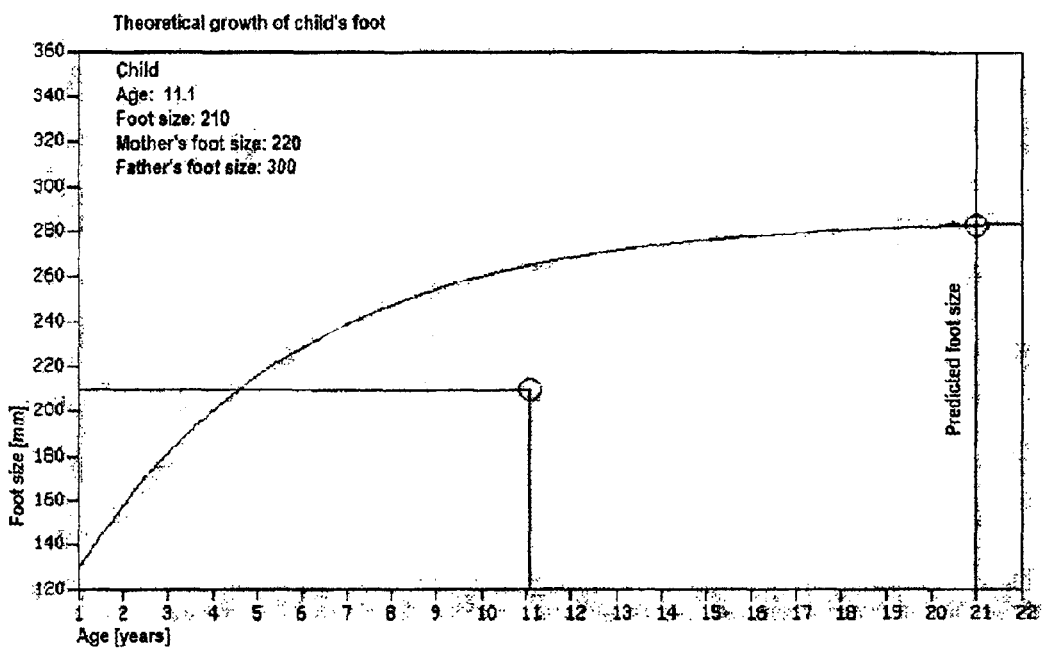

The attached drawings serve for the closest approximation of the essence of the device, representing FIG. 1—block diagram A system for predicting the period for children to safely wear newly acquired footwear in sample design; and FIG. 2 a graph of the theoretical growth of a child's foot.

SAMPLE DESIGN

A system for predicting the period for children to safely wear newly acquired footwear without the risk of damaging their growing feet according to the device in sample design is resolved as a system directly applicable at computer cash registers in the networks of shoe shops.

As is apparent from the block diagram in FIG. 1, this contains an input module 1 measuring the length of the feet and the input of information about the age of the monitored child to which is linked a prediction module 2 for the growth of children's feet implementing the laws of growth and including genetic and local influences, connected to a comparative and inferential module 3 establishing the predicted course of growth in the foot length of the monitored child. Linked to the comparative and inferential module 3 then is the output module 4 determining the nearest date for the necessary replacement of shoe size for the monitored child.

The implemented laws of growth for the prediction module 2 is the growth module for children's feet on the basis of the Carlsberg growth model, which is derived empirically from analyses of the sole lengths of children's feet in relation to the age of these children, performed at groups of 2000 children aged from 3 to 18 years.

When processing the measured data, the multiple linear regression method was used, whereas two values were applied as independent variables: the age of the child and the total length of the parent's feet. An independent variable was the child's foot length. On the basis of multiple linear regression, values were then calculated from which it is possible to compile a prediction equation of the general character:

$$Y = A1 + A2*X1 + A3*X2 \quad (1)$$

Individual statistical characteristics were determined independently for a sub-group of boys and a sub-group of girls. Later, these values were used for establishing preliminary parameter vectors.

For increasing the precision of the model, the results were consolidated from all age categories and a total group acquired the divided according to gender into subgroups of boys and girls. A decimal of the model equation was tested in various modifications and subsequently selected and gradually tested were the multiple linear regression equations below:

$$Y = A1 + A2*X1 + A3*X2 + A4*X1*X1 + A5X2*X2 \quad (2)$$

$$Y = A1 + A2*X1 + A3*X2 + A4*X1*X1 + A5*X2*X2 + A6*X1*X2 \quad (3)$$

$$Y = A1 + A2*X1 + A3*X1*X1 + A4*X2*X2 + A5*X1*X2 \quad (4)$$

$$Y = A1 + A2*X1 + A3*X1*X1 + (X2-257,4)*A4 \quad (5)$$

$$Y = A1 + A2*X1/(1 + A3*X1) + (X2-257,4)*A4 + A5*X1*X2 \quad (6)$$

(Note: 257.4 is the average value of independent variable X2)

An example of the values of the coefficients of the equations for the sub-group of girls is displayed in the following Table 1:

TABLE 1

Values of coefficients for equations for the sub-group of girls

| Coefficient | Equation number 1 | Equation number 2 | Equation number 3 | Equation number 4 | Equation number 5 | Equation number 6 |
|---|---|---|---|---|---|---|
| A1 | 12.08 | 159.8 | −120.3 | 58.06 | 44.87 | −99.22 |
| A2 | 7.14 | 12.55 | 3.2 | 10.2 | 12.55 | 56.76 |
| A3 | 0.25 | −0.41 | 0.17 | −0.27 | −0.23 | 0.12 |
| A4 | — | −0.23 | 9.74 | 0.002 | 0.23 | −0.43 |
| A5 | — | 0.0008 | 9.0 | 0.004 | — | −0.008 |
| A6 | — | — | 0.007 | — | — | — |

The acquired empirical model in the form of the arrangement of regressive equations may be used for establishing the period during which it is possible to wear newly purchased children's footwear so that this would not lead to the possible damage to the growing feet of the child due to tightness of the internal dimensions of the footwear. This is derived from the principles of the sole structure of children's footwear in the area of toe overhang, which is constructed in such a way that it would enable not only a shift in the toes toward the tip when walking during the movement phases, but also a sufficient reserve for foot growth in the scope of a single half-size. In our conditions, where the metric system is used, this is 5 mm. In Germany and in the majority of countries of Western Europe, the French system is used, which is based on grades of 6.6 mm. In this connection, it is necessary to note that the resulting numbering of footwear corresponds to the aforementioned values only in those cases when the equipment and forms comply with the sizing system. A footwear manufacturer is always oriented only on one size system, and if the customer demands shoes in another size system, this merely involves renumbering, which in itself brings a generally tolerated risk of uneven deviations from the experienced sizes. Another complicating phenomenon is the unequal growth in the length of children's feet. In the course of the creation of the empirical model, sufficiently similar longitudinal studies could be found for the growth of children's foot length. From practice, however, it is known that the growth in children's feet show certain elements of fluctuation from the curve describing the long-term growth of the feet of individual subjects or acquired from values of a greater number of individuals. Studies that have been conducted at children in nursery school have confirmed the existence of two characteristic stages of growth: acceleration and retardation.

The input module 1 measuring foot sizes and the input of information about the age of the monitored child by the system according to the device contains, in sample design, a submodule for data storage G, which is linked to the prediction module 2 for the growth of a child's feet.

The growth model for children's feet implemented in the prediction module 2 is continuously revised by the output submodel for genetic influences, the input for which are parameters for the length of the child's parent's feet. Furthermore, the growth model for children's feet, implemented in the prediction module 2, continuously revised at the same time by the output submodule 6 for local influences, connected to the submodule for data storage V of the input module L The entire system according to the device was drawn up in sample design in a simple form for the purpose of easy applicability during practical shoe sales.

Displayed below is an illustrative example of the application of the system. After its release, it is necessary to initially specify the gender and foot length of the mother and father. In both cases, it is necessary to show foot length in mm, which corresponds to the system of marking shoe lengths in Mondopoint, which is more universal. Other data relates to the age of the child. For establishing deviations for the actual sizes of children's feet from those anticipated, a presentation is required for the determined actual foot sizes of the child. For processing all data, it is possible to establish recommended period after which the next visit to a shop is nearest. Supplemental data shows how the foot size of a child will probably be in adulthood.

Furthermore, FIG. 2 shows a graph of the theoretical course of growth in child's foot length, for which input characteristics were provided. Displayed in the figure is the case of a boy aged 11.1 years, whose mother has a foot size of 220 and the father 300 (Mondopoint). As of today's theoretical date, the purchase of shoes was determined in a foot size of 210 mm. After completing foot growth, according to the prediction model, this boy will have a foot size of 284 mm. If he theoretically purchased new shoes, his feet would grow to the next size in 0.55 of a year. In a more perfect version of the system, this forecast may be designated in weeks and corresponding months. In this case, then, the result would be the 4th week of April 1996. These conditions depict a typical situation when the actual foot size is delayed against the anticipated growth probability.

The invention claimed is:

1. A prediction system of the period for safely wearing newly acquired footwear for children without the risk of damaging their growing feet, the system comprising:
   an input module measuring sole length and input of information about the age of a monitored child and a date on which shoes were purchased for the monitored child, to which module is linked a prediction module of the growth of a child's feet implementing the laws of growth on the basis of the Carlberg growth model, including an empirical model originating from an analysis of child's foot length in connection with the age of children, performed on a group of at least 2000 children connected to a comparative and inferential module establishing a predicted course of sole length growth of the monitored child to which then is linked an output module designating a date when it will be necessary to stop using the purchased shoes.

2. The prediction system defined in claim 1, wherein the empirical model for growth of a child's foot length by the prediction module includes the foot length of the child's parents as another parameter.

3. The prediction system defined in claim 1, wherein the input module measuring foot size and the input of information about the age of the monitored child contains a submodule for data storage which is connected to the prediction module for growth of the child's feet.

4. The prediction system defined in claim 1, wherein the empirical model for the growth of children's feet implemented in the prediction module is continuously revised by the output submodule with genetic influences, the input of which include in particular the length parameters of the children's parents.

5. The prediction system defined in claim 1 wherein the growth model for children's feet implemented in the prediction module is continuously revised by inputs to the submodule of local influences connected to the submodule for data storage of the input module.

6. The prediction system defined in claim 1, wherein additional output of the comparative and inferential module establishing the predicted course of foot length growth of the monitored child are data about the lengths of the child's parent's feet.

* * * * *